United States Patent
Fischler

(10) Patent No.: US 11,751,890 B2
(45) Date of Patent: Sep. 12, 2023

(54) DRILLING PLATFORM TOOL FOR SURGERIES

(71) Applicant: MED-EL Elektromedizinische Geraete GmbH, Innsbruck (AT)

(72) Inventor: Wolfgang Fischler, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 514 days.

(21) Appl. No.: 16/651,202

(22) PCT Filed: Oct. 5, 2018

(86) PCT No.: PCT/US2018/054633
§ 371 (c)(1),
(2) Date: Mar. 26, 2020

(87) PCT Pub. No.: WO2019/071141
PCT Pub. Date: Apr. 11, 2019

(65) Prior Publication Data
US 2021/0196289 A1      Jul. 1, 2021

Related U.S. Application Data

(60) Provisional application No. 62/585,717, filed on Nov. 14, 2017, provisional application No. 62/569,023, filed on Oct. 6, 2017.

(51) Int. Cl.
*A61B 17/17*   (2006.01)
*A61N 1/05*    (2006.01)
(Continued)

(52) U.S. Cl.
CPC ...... *A61B 17/1739* (2013.01); *A61B 17/1703* (2013.01); *A61N 1/0541* (2013.01);
(Continued)

(58) Field of Classification Search
CPC ......... A61B 34/20; A61B 34/10; A61B 90/10; A61B 90/11; A61B 17/0218;
(Continued)

(56) References Cited

U.S. PATENT DOCUMENTS

2005/0216032 A1   9/2005  Hayden
2009/0149890 A1   6/2009  Martin
(Continued)

FOREIGN PATENT DOCUMENTS

AU   2015221540 A1   9/2015
CA   2 985 664        12/2016
(Continued)

OTHER PUBLICATIONS

International Searching Authority/US, International Search Report and Written Opinion of the International Searching Authority, Application No. PCT/US2018/054633, dated Jan. 29, 2019, 18 pages.
(Continued)

*Primary Examiner* — Marcela I. Shirsat
(74) *Attorney, Agent, or Firm* — Burns & Levinson, LLP; Alexander J. Smolenski, Jr.

(57) ABSTRACT

A surgical guide tool and methodology includes a non patient-specific platform including one or more supports for attaching to a body part of a subject. A non patient-specific block has a top planar surface and a bottom planar surface, and includes a guide aperture extending from the top planar surface to the bottom planar surface for guiding a surgical instrument in making at least one of a cut and a drill hole. An intermediate module is removably positioned between the platform and the block. The intermediate module has patient-specific dimensions such that the guide aperture has a desired alignment relative to the body part when the surgical guide tool is attached to the body part of the patient
(Continued)

and the intermediate module is positioned between the platform and the block.

12 Claims, 9 Drawing Sheets

(51) Int. Cl.
*A61B 17/34* (2006.01)
*A61B 34/10* (2016.01)
*A61B 17/02* (2006.01)

(52) U.S. Cl.
CPC ....... *A61B 17/0218* (2013.01); *A61B 17/1771* (2016.11); *A61B 17/3403* (2013.01); *A61B 2017/3407* (2013.01); *A61B 2034/108* (2016.02)

(58) Field of Classification Search
CPC . A61B 17/1771; A61B 17/1739; A61B 17/17; A61B 17/1703; A61B 2017/3403; A61B 2017/3405; A61B 2017/3407; A61B 2090/101; A61B 2090/103; A61B 2034/108; A61B 1/05; A61B 17/3403; A61N 1/0541
USPC .................................................. 606/130, 129
See application file for complete search history.

(56) References Cited

U.S. PATENT DOCUMENTS

| | | | |
|---|---|---|---|
| 2010/0094311 | A1 | 4/2010 | Jolly et al. |
| 2012/0141572 | A1 | 6/2012 | Hessler et al. |
| 2013/0053867 | A1* | 2/2013 | Gowda ................. A61B 90/11 606/130 |
| 2013/0274778 | A1 | 10/2013 | Mercier et al. |
| 2014/0107715 | A1 | 4/2014 | Heilman et al. |
| 2014/0162213 | A1 | 6/2014 | Haber |
| 2015/0359553 | A1 | 12/2015 | Harnisch |
| 2016/0242934 | A1 | 8/2016 | van der Walt et al. |
| 2018/0008367 | A1* | 1/2018 | Rau ........................ A61B 17/17 |
| 2018/0110568 | A1* | 4/2018 | Lenarz .................. A61B 90/11 |

FOREIGN PATENT DOCUMENTS

| | | |
|---|---|---|
| CN | 101878002 A | 11/2010 |
| CN | 103764048 A | 4/2014 |
| WO | 2011057032 A2 | 5/2011 |
| WO | WO 2012/158254 A2 | 11/2012 |

OTHER PUBLICATIONS

European Patent Office, Extended European Search Report, Application No. 18864083.3, dated May 27, 2021, 10 pages.
China National Intellectual Property Administration, Supplementary Search Report, Application No. 201880064878 8, dated Oct. 30, 2022.

\* cited by examiner

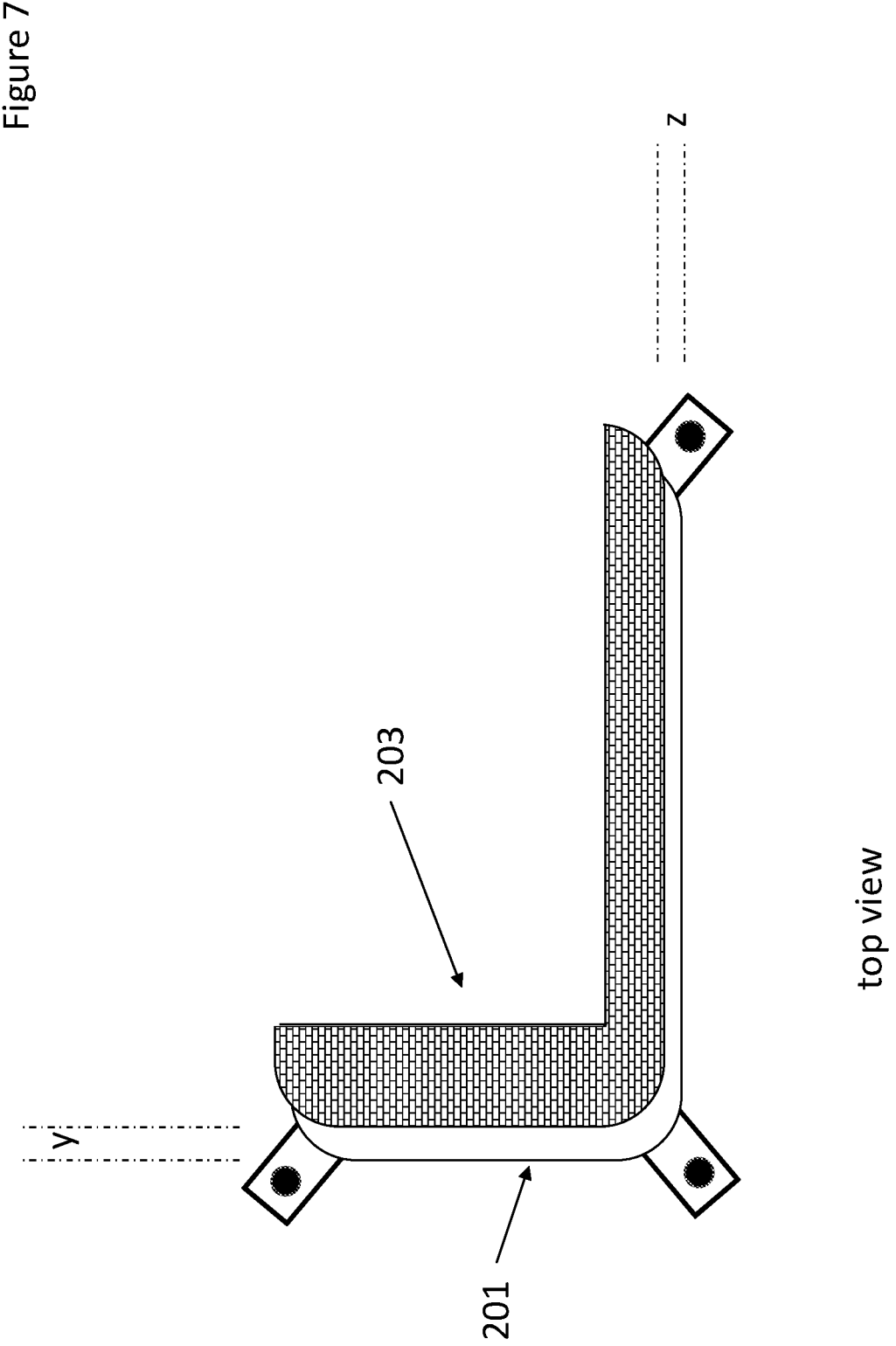

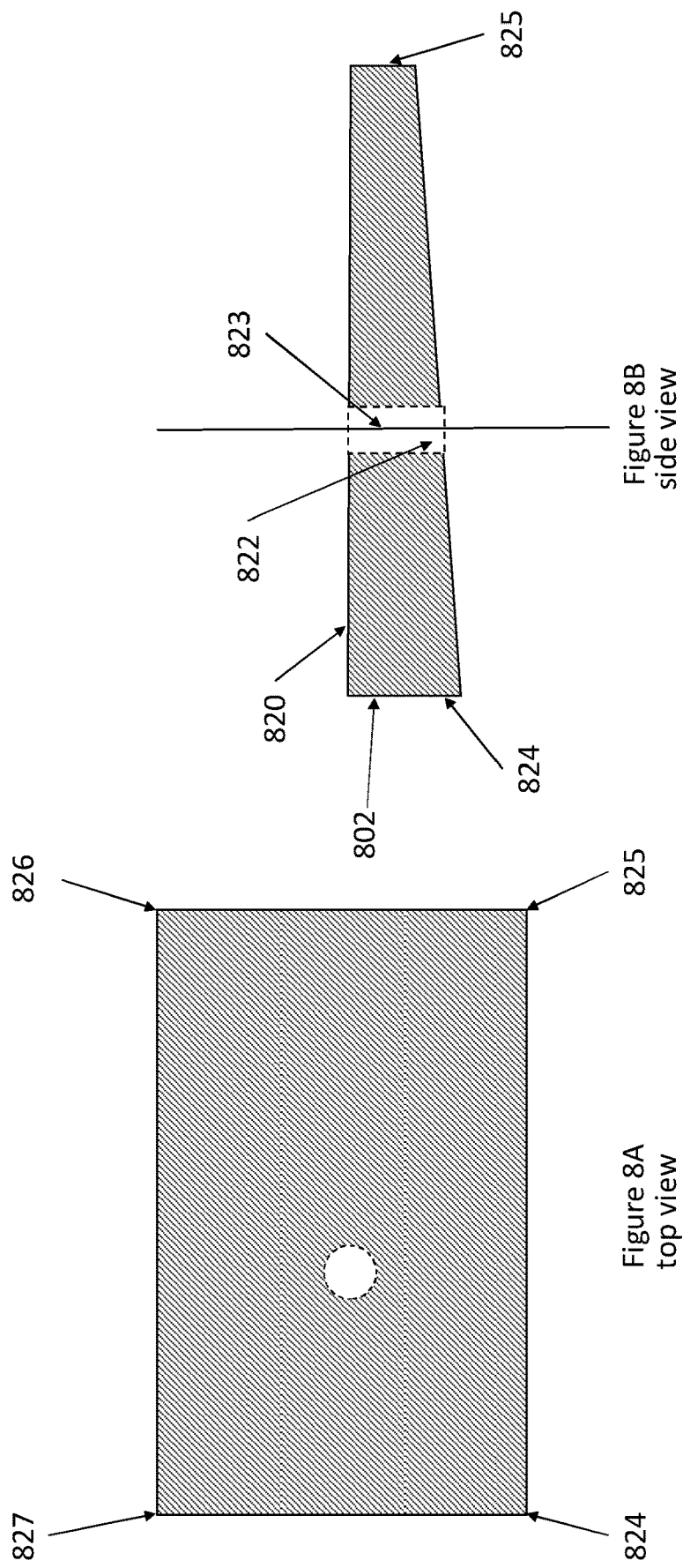

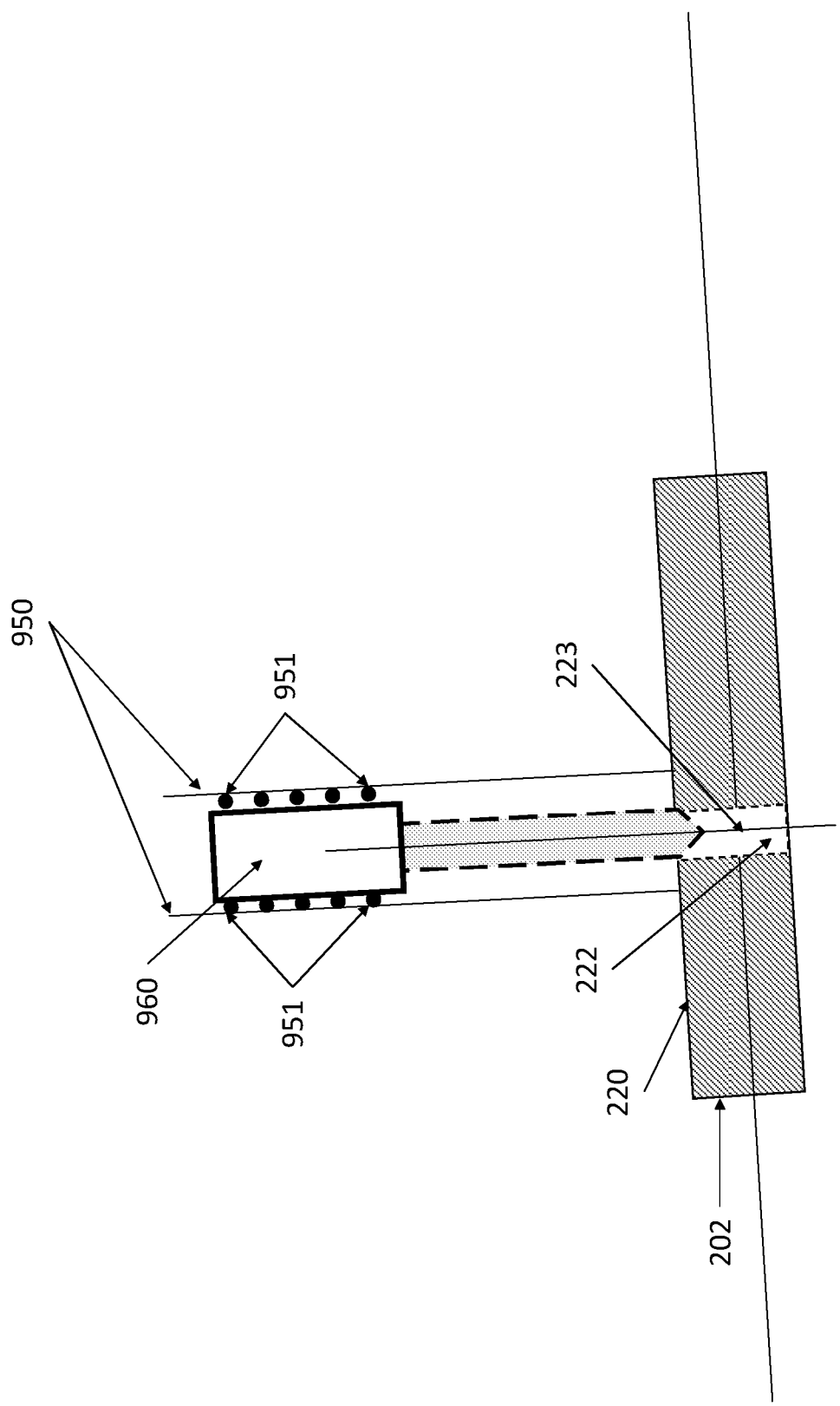

DRILLING PLATFORM TOOL FOR SURGERIES

CROSS-REFERENCE TO RELATED APPLICATIONS

This application is a 371 national phase entry of Patent Cooperation Treaty Application PCT/US2018/054633, filed Oct. 5, 2018, which in turn claims priority from both U.S. Provisional Patent 62/569,023, filed Oct. 6, 2017, and U.S. Provisional Patent 62/585,717, filed Nov. 14, 2017. Each of the above described applications is incorporated herein by reference in their entireties.

TECHNICAL FIELD

The present invention relates to a surgical tool and methodology for guiding surgical instruments, and more particularly, to a drilling platform tool that provides a well-defined drilling or cutting path.

BACKGROUND ART

Many surgeries require that the surgeon perform drilling and/or cutting through bone or other body parts. For example, some patients may have hearing loss in one or both ears that is too severe to be helped by hearing aids, and can benefit from a cochlear implant. To insert the cochlear implant, the surgeon typically has to perform surgical operations that require drilling into the middle ear.

A normal ear transmits sounds as shown in FIG. 1 through the outer ear 101 to the tympanic membrane (eardrum) 102, which moves the bones of the middle ear 103 (malleus, incus, and stapes), which in turn vibrate the oval window and round window openings of the cochlea 104. The cochlea 104 is a long narrow duct wound spirally about its axis for approximately two and a half turns. The cochlea 104 includes an upper channel known as the scala vestibuli and a lower channel known as the scala tympani, which are connected by the cochlear duct. The scala tympani forms an upright spiraling cone with a center called the modiolar where the spiral ganglion cells of the acoustic nerve 113 reside. In response to received sounds transmitted by the middle ear 103, the fluid-filled cochlea 104 functions as a transducer to generate electric pulses that are transmitted to the cochlear nerve 113, and ultimately to the brain.

Hearing is impaired when there are problems in the ability to transduce external sounds into meaningful action potentials along the neural substrate of the cochlea. In such cases a cochlear implant is an auditory prosthesis which uses an implanted stimulation electrode to bypass the acoustic transducing mechanism of the ear and instead stimulate auditory nerve tissue directly with small currents delivered by multiple electrode contacts distributed along the electrode.

FIG. 1 also shows some components of a typical cochlear implant system which includes an external microphone that provides an audio signal input to an external signal processing stage 111 where various signal processing schemes can be implemented. The processed signal is then converted into a digital data format, such as a sequence of data frames, for transmission into the implant stimulator 108. Besides extracting the audio information, the implant stimulator 108 also performs additional signal processing such as error correction, pulse formation, etc., and produces a stimulation pattern (based on the extracted audio information) that is sent through connected wires 109 to an electrode array 110 inserted into the cochlea. Typically, this electrode array 110 includes multiple electrode contacts on its surface that provide selective stimulation of the cochlea 104. Stimulation is either carried out against an external reference electrode contact (i.e., a remote ground contact) outside the cochlea or against another electrode contact of the array within the cochlea 104.

The insertion of the electrode array 110 often includes making an incision behind the ear, and using a drill to then enter the middle ear. The electrode array 110 is placed through an opening created in the cochlea 104, and the implant stimulator 108 is then placed into a pocket under the skin on the skull behind the ear.

Various prior art devices have been proposed that assist the surgeon in making such precise surgical drill holes or other cuts. U.S. Pat. No. 7,981,122 to Labadie et al. discloses various surgical guide tools that include a guide platform having legs of adjustable lengths that rest on a body part. However, the assembly and adjustment of the positioning of the legs on the body part can be time-consuming and expensive. To avoid disadvantages of having adjustable legs, WO2016/198032 (Horsys Gmbh) proposes a positioning aid with legs that cannot be changed in length. The guide plate in WO2016/198032 is manufactured for each patient according to produced pre-operative images, whereas the other components of the system may be reusable. In WO2016/198032, the calculated optimal drilling trajectory is enabled by providing a guide plate having a center and an axis perpendicular to the surface of the plate and through which a trajectory may be drilled off-center and under a certain angle to the axis. This may not be optimal, as the surgeon may thus have to move a drill oriented at an angle other than perpendicular from the surface of the plate. Each of the above cited references is hereby incorporated herein by reference in its entirety.

SUMMARY OF THE EMBODIMENTS

In accordance with an embodiment of the invention, a surgical guide tool includes a non patient-specific platform including one or more supports for attaching to a body part of a subject. A non patient-specific block has a top planar surface and a bottom planar surface, and includes a guide aperture extending from the top planar surface to the bottom planar surface for guiding a surgical instrument in making at least one of a cut and a drill hole. An intermediate module is removably positioned between the platform and the block. The intermediate module has patient-specific dimensions such that the guide aperture has a desired alignment relative to the body part when the surgical guide tool is attached to the body part of the patient and the intermediate module is positioned between the platform and the block.

In accordance with related embodiments of the invention, the guide aperture may be a borehole defining an axis through the block. The axis may be perpendicular to both the top and bottom planar surfaces of the block.

In accordance with further related embodiments of the invention, the intermediate module may have a top module surface for positioning adjacent the block, and a bottom module surface for positioning adjacent the platform, the intermediate module having a varying height between the top surface and the bottom surface such that the guide aperture has a desired alignment relative to the body part when the surgical guide tool is attached to the body part of the patient. The top module surface and the bottom module surface may be planar and non-parallel.

In accordance with still further related embodiments of the invention, the supports of the platform may include legs that are fixed and immobile relative to the platform, the legs having non-adjustable dimensions. Both the intermediate module and the platform may be configured so that they do not block the aperture in the block when the intermediate module is positioned between the platform and the block. The block may be braced to the platform such that there is no freedom of play in one or more dimensions. The surgical tool may further include a clamp, for clamping the platform, block and/or intermediate module to each other. The platform, block and/or intermediate module may include one of an elevation, a recess, a pin, and/or a pin receptacle, to ensure proper positioning relative to each other.

In accordance with another embodiment of the invention a method includes providing a non patient-specific platform for attaching to a body part of a subject. A non patient-specific block is provided having a top planar surface and a bottom planar surface, the block including a guide aperture extending from the top planar surface to the bottom planar surface for guiding a surgical instrument. Electronic image data is obtained of an anatomical area of the subject. A trajectory for at least one of a cut and a drill hole is determined based, at least in part, on the electronic image data. An intermediate module is provided that is configured to be removably positioned between the platform and the block, the intermediate module having patient-specific dimensions such that the guide aperture in the block is configured to guide the surgical instrument in making the at least one of a cut and drill hole along the determined trajectory when the platform is attached to the body part of the patient and the intermediate module is sandwiched between the platform and the block.

In accordance with related embodiments of the invention, obtaining the electronic image data may include one of pre-operatively, intraoperatively, optically, an Mill, a CT and a spiral CT, or combinations thereof.

In accordance with further related embodiments of the invention, the method may further include mounting the platform on the body part, with the intermediate module sandwiched between the platform and the block, and using the guide aperture to make at least one of a cut and a drill hole into the body part. The body part may be the skull, wherein the platform is mounted on the skull, and wherein the guide aperture is used in guiding a surgical instrument to drill a hole through the skull into the middle ear, the method further including inserting an electrode array of a cochlear implant into the hole.

In accordance with still further related embodiments of the invention, the intermediate module may have a top module surface for positioning adjacent the block, and a bottom module surface for positioning adjacent the platform, the intermediate module having a varying height between the top surface and the bottom surface such that the guide aperture has the desired alignment relative to the body part when the surgical guide tool is attached to the body part of the patient and the intermediate module is positioned between the platform and the block. The top module surface and the bottom module surface may be planar and non-parallel.

In accordance with yet further related embodiments of the invention, the guide aperture may be a borehole defining an axis through the block. The axis may be perpendicular to both the top and bottom planar surfaces of the block. The platform may include legs for attaching to the body part, the legs being fixed and immobile relative to the platform, the legs having fixed dimensions that cannot be varied. Both the intermediate module and the platform do not block the aperture in the block when the intermediate module is sandwiched between the platform and the block. Providing the intermediate module may include cutting, drilling, milling, and/or laser sintering a blank of material.

In accordance with another embodiment of the invention, a surgical guide tool includes a non patient-specific platform including one or more supports for attaching to a body part of a subject. A patient-specific block has a top surface and a bottom surface, the block including a guide aperture extending from the top surface to the bottom surface for guiding a surgical instrument in a making at least one of a cut and a drill hole. The block has patient-specific dimensions such that the guide aperture has a desired alignment relative to the body part when the surgical guide tool is attached to the body part of the patient and the block is braced against the platform. The top surface and the bottom surface of the block are planar and non-parallel.

In accordance with related embodiments of the invention, the guide aperture may be a bore hole defining an axis through the block. There may be a non patient-specific, predefined arrangement between the axis and the top surface of the block. Illustratively, there may be a non patient-specific, predefined angle between the axis of the guide aperture and the top surface of the block, wherein the height between the top surface and the bottom surface of the block varies such that the angle is at the desired alignment relative to the body part when the surgical guide tool is attached to the body part of the patent and the block is braced against the platform. The axis may be perpendicular to the top surface of the block. The supports of the platform include non patient-specific legs that are fixed and immobile relative to the platform, the legs having non-adjustable dimensions. When the block is braced to the platform there may be no freedom of play in one or more dimensions. The surgical tool may include a clamp for clamping the block to the platform. The block and/or platform may include an elevation, a recess, a pin, and/or a pin receptacle, to ensure proper positioning of the block relative to the platform.

In accordance with another embodiment of the invention, a method includes providing a non patient-specific platform for attaching to a body part of a subject. Electronic image data is obtained of an anatomical area of the subject. A trajectory for making at least one of a cut and a drill hole is determined based, at least in part, on the electronic image data. A patient-specific block is provided having a top surface and a bottom surface, the block including a guide aperture extending from the top surface to the bottom surface for guiding a surgical instrument in making at least one of a cut and a drill hole. The top surface and the bottom surface of the block are planar and non-parallel.

In accordance with related embodiments of the invention, obtaining the electronic image data may include one of pre-operatively, intraoperatively, optically, an Mill, a CT and a spiral CT, or combinations thereof.

In accordance with further related embodiments of the invention, the method may further include mounting the platform on the body part, with the block braced against the platform. The guide aperture is used to make at least one of a cut and a drill hole into the body part. The body part may be the skull, wherein the platform is mounted on the skull, and wherein the guide aperture is used in guiding a surgical instrument to drill a hole through the skull into the middle ear, the method further including inserting an electrode array of a cochlear implant into the hole.

In accordance with still further embodiments of the invention, the block may be braced to the platform such that there is no freedom of play in one or more dimensions. The guide aperture may be a bore hole defining an axis through the block. There may be a non patient-specific, predefined arrangement between the axis and the top surface of the block. Illustratively, there may be a non patient-specific, predefined angle between the axis of the guide aperture and the top surface of the block, wherein the height between the top surface and the bottom surface of the block varies such that the angle is at the desired alignment relative to the body part when the surgical guide tool is attached to the body part of the patient and the block is braced against the platform. The axis may be perpendicular to the top surface of the block. The platform may include non patient-specific legs for attaching to the body part, the legs being fixed and immobile relative to the platform, the legs having fixed dimensions that cannot be varied. Providing the block may include cutting, drilling, milling, and/or laser sintering a blank of material. The block may be clamped to the platform. The block and/or platform may include one of an elevation, a recess, a pin, and a pin receptacle, or combinations thereof, to ensure proper positioning of the block relative to the platform.

In accordance with embodiments related to the above-described embodiments, the surgical guide tool may include a guiding element that may be attached or integral with the block. The guiding element may have guiding walls, with, for example, rollers operatively coupled to the guiding walls. When making the drill hole or cut, the surgical instrument contacts the rollers to ensure that the surgical instrument moves through the guide aperture without tilt.

BRIEF DESCRIPTION OF THE DRAWINGS

The foregoing features of embodiments will be more readily understood by reference to the following detailed description, taken with reference to the accompanying drawings, in which:

FIG. 4A shows a top view of a platform in accordance with an embodiment of the invention, while FIG. 4B shows a side view of the platform;

FIG. 5A shows a top view of the intermediate module 203, in accordance with an embodiment of the invention, while FIG. 5B shows a side view of the intermediate module 203;

FIG. 7 shows lateral offsets y and z between the platform and intermediate module, in accordance with an embodiment of the invention; and FIGS. 8A (top view) and 8B (side view) show a patient specific block of a surgical guidance tool that does not have intermediate module, in accordance with an embodiment of the invention.

FIG. 9 shows a guiding element, in accordance with an embodiment of the invention.

DETAILED DESCRIPTION OF SPECIFIC EMBODIMENTS

In illustrative embodiments of the invention, a surgical guide tool and methodology for guiding a surgical instrument in making a cut and/or drill holes in a body of a subject is provided. In an exemplary embodiment, the surgical guide tool may be used when drilling into the skull of a patient, and more particularly, to drill a hole in the middle ear facilitating insertion of an electrode array of a cochlear implant. Note however, that the provided surgical tool and methodology is not limited to the skull, and may also be applied to other parts of the body. Details hereto are described below.

Figure 2:
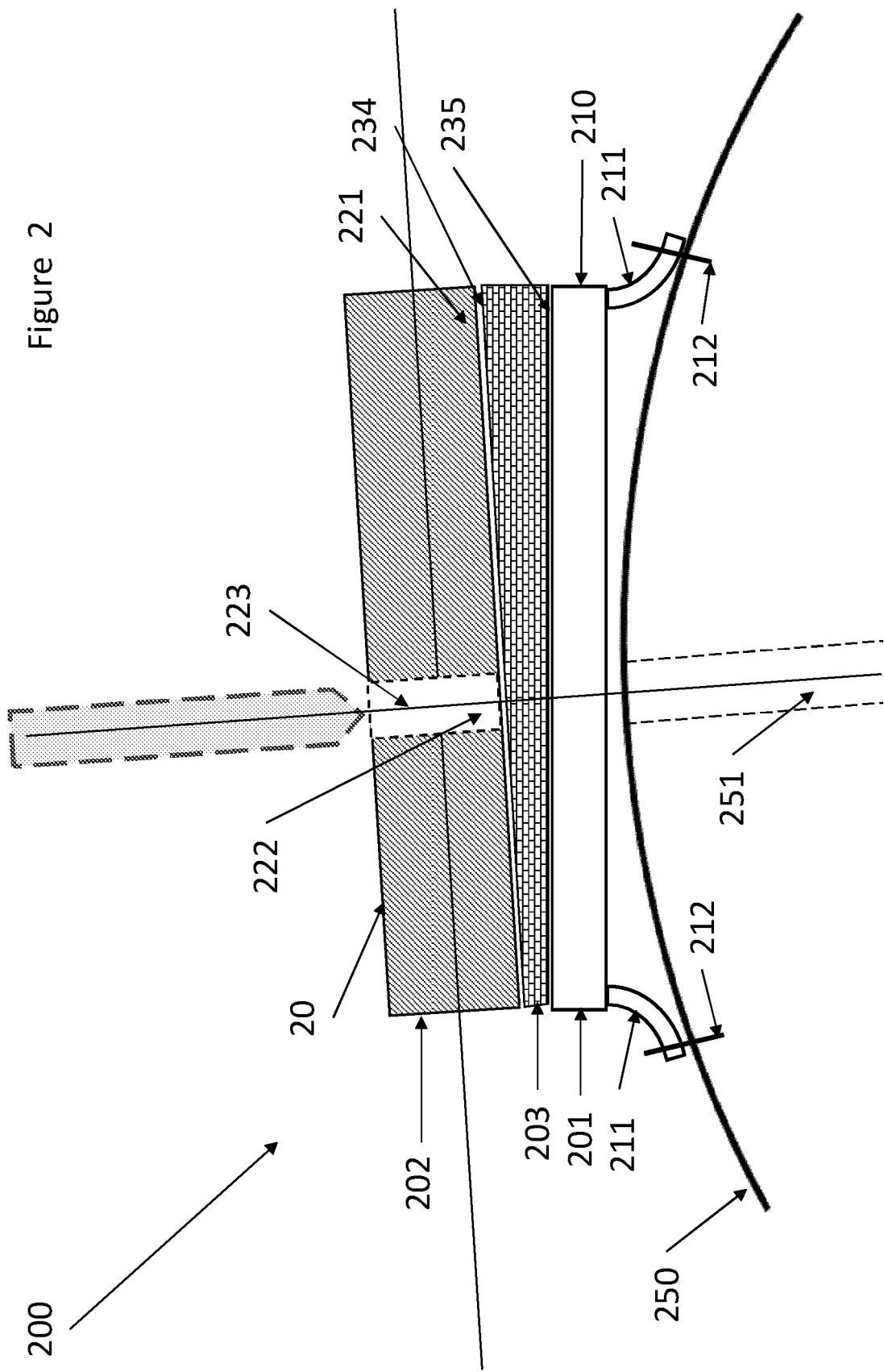
FIG. 2 shows a composite view of a surgical guide tool, in accordance with an embodiment of the invention.
Figure 3:
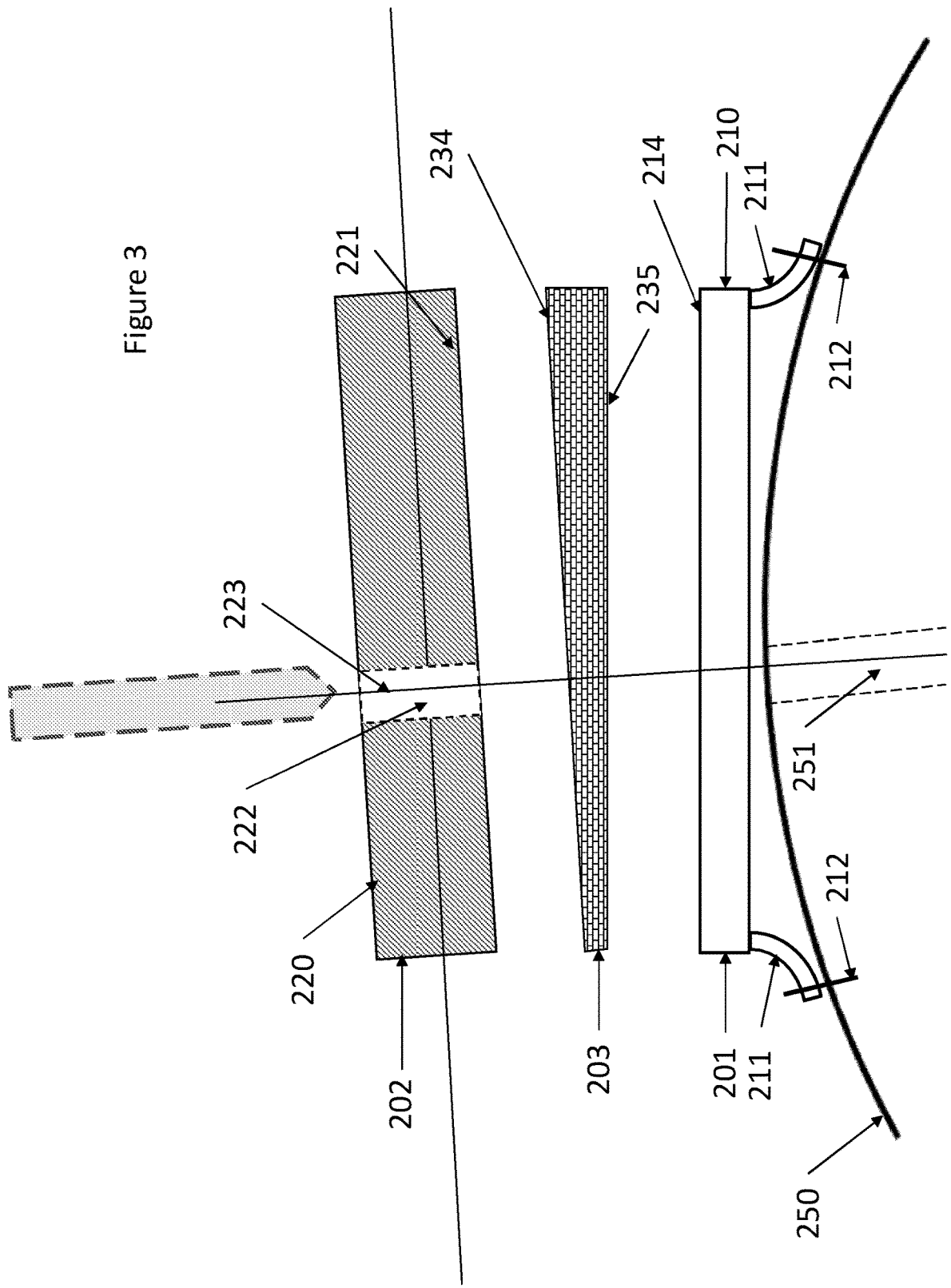
FIG. 3 shows an exploded view of the surgical guide tool depicted in FIG. 2.

FIG. 2 shows a composite view of a surgical guide tool 200, in accordance with an embodiment of the invention. FIG. 3 shows an exploded view of the surgical guide tool 200 depicted in FIG. 2.

The surgical guide tool 200 includes a non patient-specific platform 201 having a plate 210. One or more supports 211 may be fixed to the plate 210, the support(s) 211 for attaching to a body part 250 of a subject. The support(s) 211 may include, without limitation, one or more legs 211. The legs 211 may have fixed dimensions and shape that cannot be varied. The leg 211 may be integral with the plate 210, or attached at one end to the plate 210 with, for example, screws or welds, such that they are fixed and immobile relative to the platform 201. The other end of each leg 211 serves to rest on the body part, and may include various attachment mechanisms 212 known in the art, such as screws or pins, for fixing the legs, and hence the platform 201, to the body part 250.

FIG. 4A shows a top view of the platform 201, and FIG. 4B shows a side view of the platform 201, in accordance with an embodiment of the invention. The platform 201 may include an opening 213. The opening 213 is a cavity which leads from one side to the other of the plate 210 and may be surrounded in whole or in part by plate 210. For example, the plate 210 may have, without limitation, the shape of an L as shown in FIG. 4A. In other embodiments, the plate 210 may be circular or rectangular in form, or have other forms which support the surgical process described further below. Plate 210 has a top surface 214, upon which, for example, a block may sit on, described in more detail below.

Figure 1:
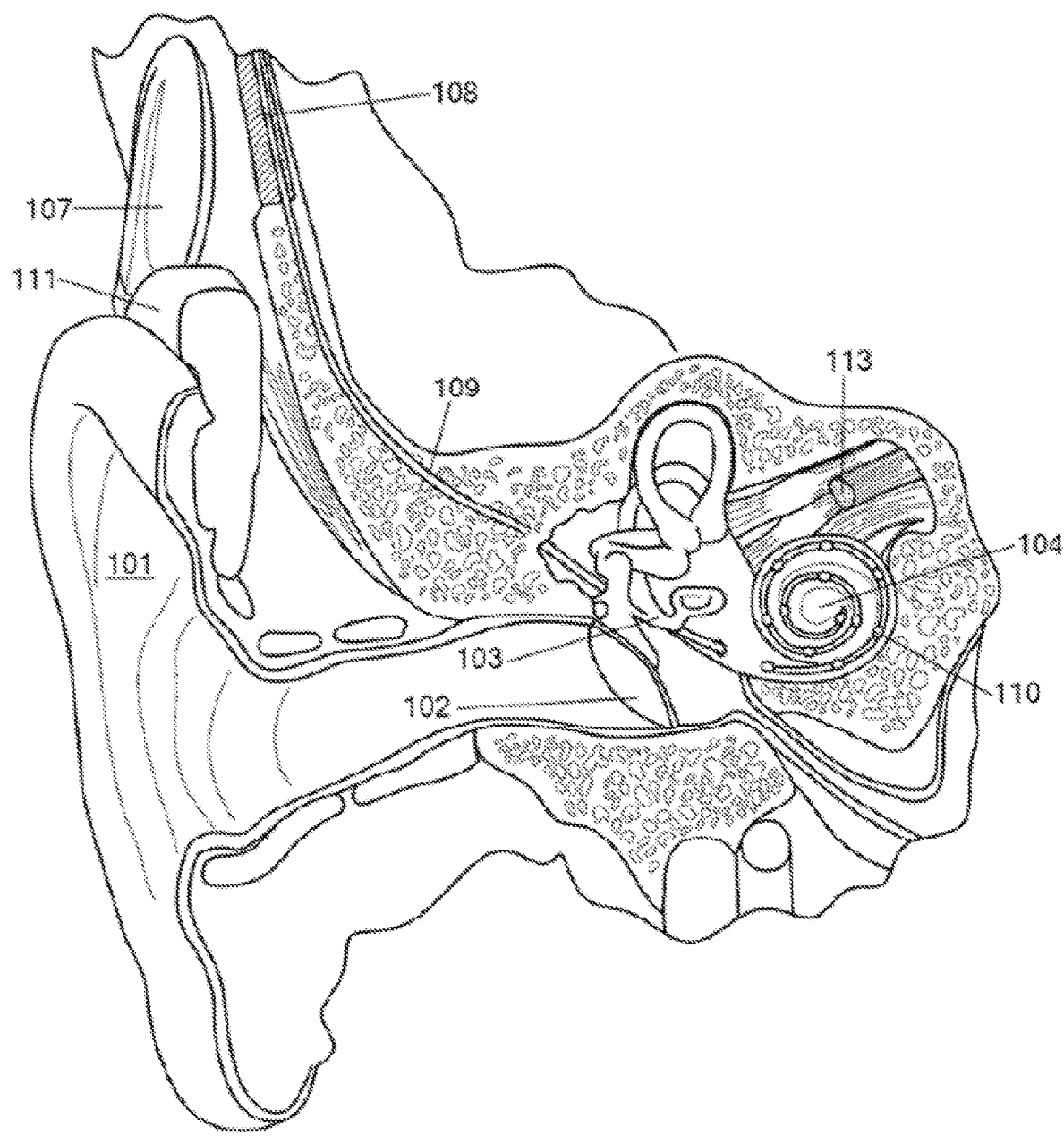
FIG. 1 shows various anatomical structures of the human ear and components of a typical cochlear implant system in relation thereto.

Referring back to FIGS. 2 and 3, the surgical guide tool 200 further includes a non patient-specific block 202 having a top planar surface 220 and a bottom planar surface 221. The bottom surface 221 of the block 202 is closer to the body part 250 when the surgical guide tool 200 is fixed to the body part 250, as shown in FIGS. 1 and 2. The block 202 includes a guide aperture 222 extending from the top planar surface 220 to the bottom planar surface 221 for guiding a surgical instrument in making at least one of a cut and a drill hole.

In illustrative embodiments of the invention, the block 202 may serve as a drilling table, with the guide aperture 222 being a borehole 222 that defines an axis 223 through the block 202. There may be a non patient-specific, predefined arrangement between the axis 223 and the top surface 220 of the block 202. For example, and without limitation, the axis 223 may be perpendicular to both the top and bottom planar surfaces 220, 221 of the block 202. This may be advantageous for a surgeon, as it may often be easier to keep and move a drill oriented perpendicular to a surface than under other angles. However, the axis 223 may also be non-perpendicular to the top and bottom planar surfaces 220, 221 of the block 202. In contrast to conventional drilling tables, such as, for example, the one described in WO2016/198032, not only the non patient-specific platform 201, but also the non patient-specific block 202 may be manufactured independent of the body part 250 (e.g. the patient's skull) and may be reusable for many patients.

As shown in FIGS. 2 and 3, the surgical guide tool 200 also includes an intermediate module 203 removably sandwiched between the platform 201 and the block 202. The intermediate module 203 has patient-specific dimensions, customized to the patient, such that the guide aperture 222 has a desired alignment relative to the body part 250 when the surgical guide tool 200 is attached to the body part 250 of the patient and the intermediate module 203 is positioned between the platform 201 and the block 202. Thus, regardless of the alignment of the guide aperture 222 in the reusable, non patient-specific block 202, the patient-specific intermediate module 204 will ensure that the guide aperture 222 has the proper alignment to make the cut or drill hole.

Figure 5:
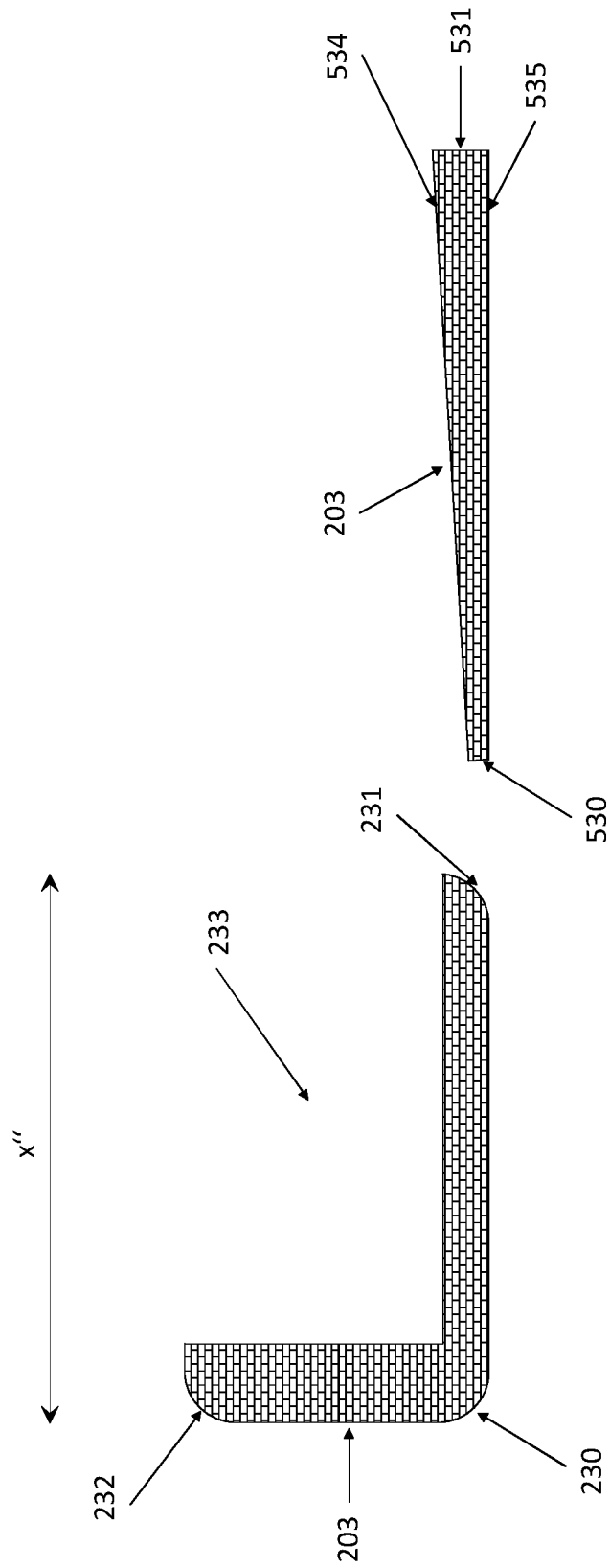

FIG. 5A shows a top view of the intermediate module 203, while FIG. 5B shows a side view of the intermediate module 203, in accordance with an embodiment of the invention. The intermediate module 203 includes a top module surface 234 for positioning proximate and/or adjacent the block 202, and a bottom module surface 235 for positioning proximate and/or adjacent the platform 201. In various embodiments, the top module surface 534 and the bottom module surface 535 are planar and non-parallel. The height between the top module surface 534 and the bottom module surface 535 may vary over the area of the intermediate module 203, such that the guide aperture 222 has a desired alignment relative to the body part 250 when the surgical guide tool 200 is attached to the body part 250 of the patient. For example, if the intermediate module 203 is L formed, at least some of the heights 530, 531, and 532 may be different (see FIGS. 5A and 5B).

From a top view, intermediate module 203 may have a different form as the plate 210, or they may have similar forms, as exemplarily shown in FIG. 5A, top view. In any case, the intermediate module 203 has an opening 233 which borders should not cover opening 213 of plate 210 when the platform 201 and intermediate module 203 are adjacent each other.

While the basic form of plate 210 and intermediate module 203 may be similar, their lateral dimension may vary. This is exemplarily indicated by lengths x' of plate 210 (see FIG. 4A) and x" of intermediate module 203 (see FIG. 5A). x' may be substantially equal to x", however in various embodiments x" may also be larger than x' for reason outlined further below. Similarly, the lengths perpendicular to x' or x" may vary.

Intermediate module 203 may be manufactured interoperatively during a medical procedure as a disposable module, or may be manufactured preoperatively. As the dimensions of the intermediate module 203 are patient-specific, it is manufactured for each patient individually and may be used just once, whereupon it may be disposed. In contrast, the platform 201 and block 202 are non patient-specific, and may be used repeatedly with various patients.

Figure 6:
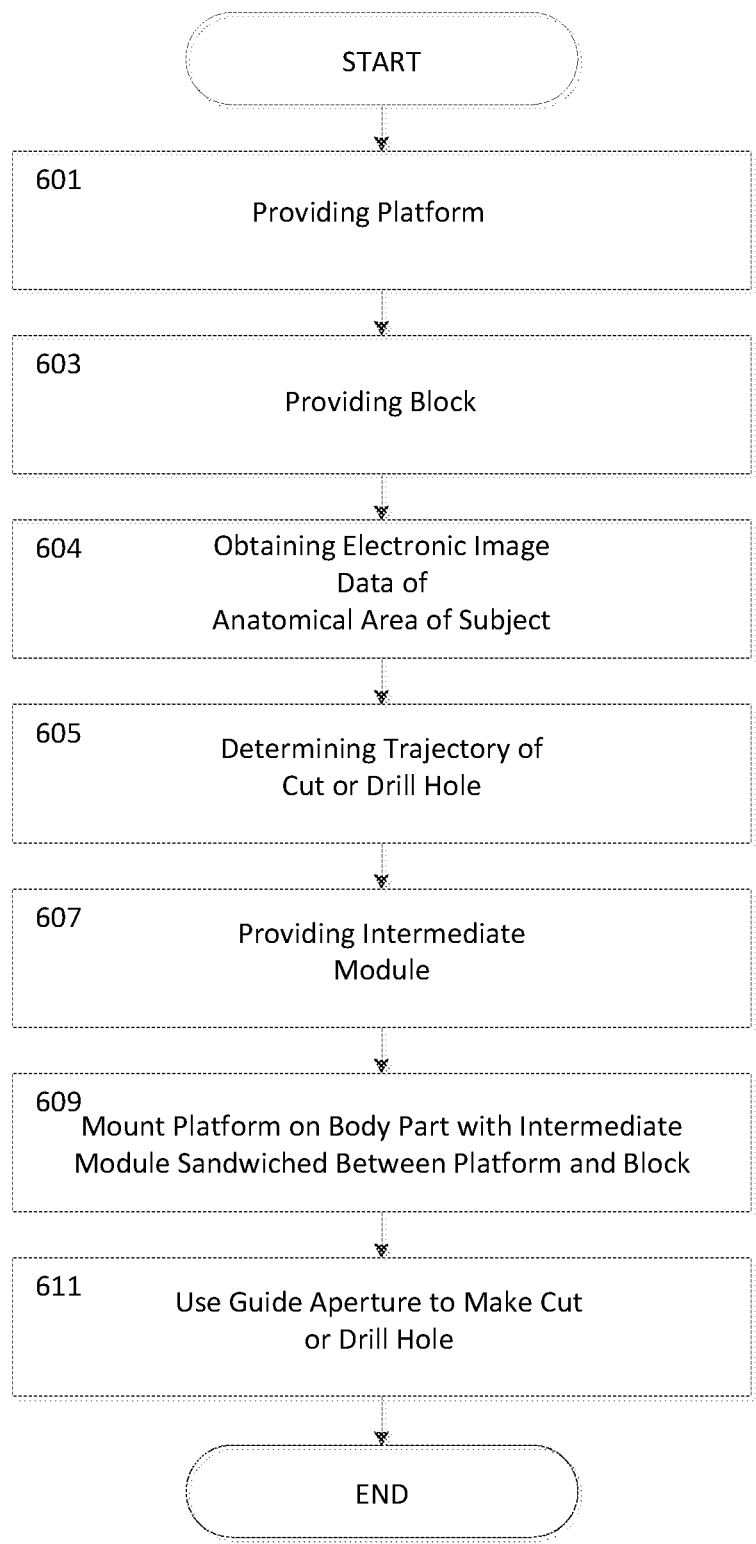
FIG. 6 is a flowchart chart illustrating a methodology that includes manufacturing an intermediate module, and further includes performing a medical procedure, in accordance with an embodiment of the invention.

FIG. 6 is a flowchart illustrating a methodology that includes manufacturing an intermediate module, and further includes performing a medical procedure, in accordance with an embodiment of the invention. The non patient-specific platform and block are provided, steps 601 and 603. A surgeon may choose from a set of platforms/plates and blocks which best suit the anatomy of the patient's body part and anatomical area of interest (for example, and without limitation, the skull). The platform may include marker elements utilized during subsequent imaging of the patient's body part and anatomical area of interest. The marker elements may be visible on the acquired image of the patient and may be advantageous in determining the position and orientation of the platform relative to the patient's area of interest.

Electronic image data of the patient's anatomical area of interest is obtained, step 604. Obtaining the electronic image data may be done intraoperatively, or alternatively, pre-operatively. Obtaining the electronic image data may include an Mill, a CT and/or a spiral CT. The electronic image data may also be obtained optically.

Based on the electronic image data, a trajectory to be cut or drilled is determined, step 605. For example, a specialized software module running on a processor may analyze the electronic image data and calculate parameters for a trajectory to be drilled. Illustratively, when inserting an electrode array of a cochlear implant, this may be the optimal trajectory from the patient's skull bone behind the ear into the middle ear. Important trajectory parameters of the trajectory may include, without limitation, its trajectory 251 (shown in FIG. 1) and the point where the axis crosses the surface of the skull.

Per these trajectory parameters, a suitable intermediate module together with its characteristic module parameters can be determined and manufactured, step 607. If the intermediate module is L shaped as shown in FIGS. 5A and B, then characteristic module parameters may include, without limitation, heights 530, 531, and 532, as well as lateral offsets y and z between the platform 201 and intermediate module 301, as exemplary shown in FIG. 7. In various embodiments, the characteristic module parameters may also include lateral offsets between intermediate module and block. Referring to FIG. 2, these offsets may be used to ensure that in the composite surgical guide tool 200, the axis 223 of bore hole 222 in the block 202 coincides with the determined trajectory 251.

A wide variety of mechanical processes may be used in manufacturing the intermediate module. These mechanical processes may include, without limitation, cutting, drilling, milling, etc. from a blank of suitable material. In other embodiments, the intermediate module may be molded.

Once the intermediate module is provided, the platform may be mounted on the body part, with the intermediate module sandwiched between the platform and the block, step 609. Illustratively, as shown in FIG. 1, a drilling platform 201 may be mounted on patient's skull bone 250 upon which the intermediate module 203 and then the drilling table 202 sits. In the composite state, with the surgical guide tool 200 mounted on the body part to perform a drilling procedure, the longitudinal axis 223 of the bore hole 222 coincides with the longitudinal axis of the desired and predetermined trajectory 251 into the skull bone 250.

The surgeon or robot may then insert a surgical instrument through the guide aperture to make the cut or drill hole, step 611. The intermediate module ensures that the trajectory or the surgical instrument follows the desired trajectory. Additionally, as described above, in various embodiments of the invention the longitudinal axis of the guide aperture in the non patient-specific block may be perpendicular to the surface of drilling table. This may be beneficial for the surgeon, as it may be easier to keep and move a drill oriented perpendicular to the surface of the block than under another angle.

Figure 4:
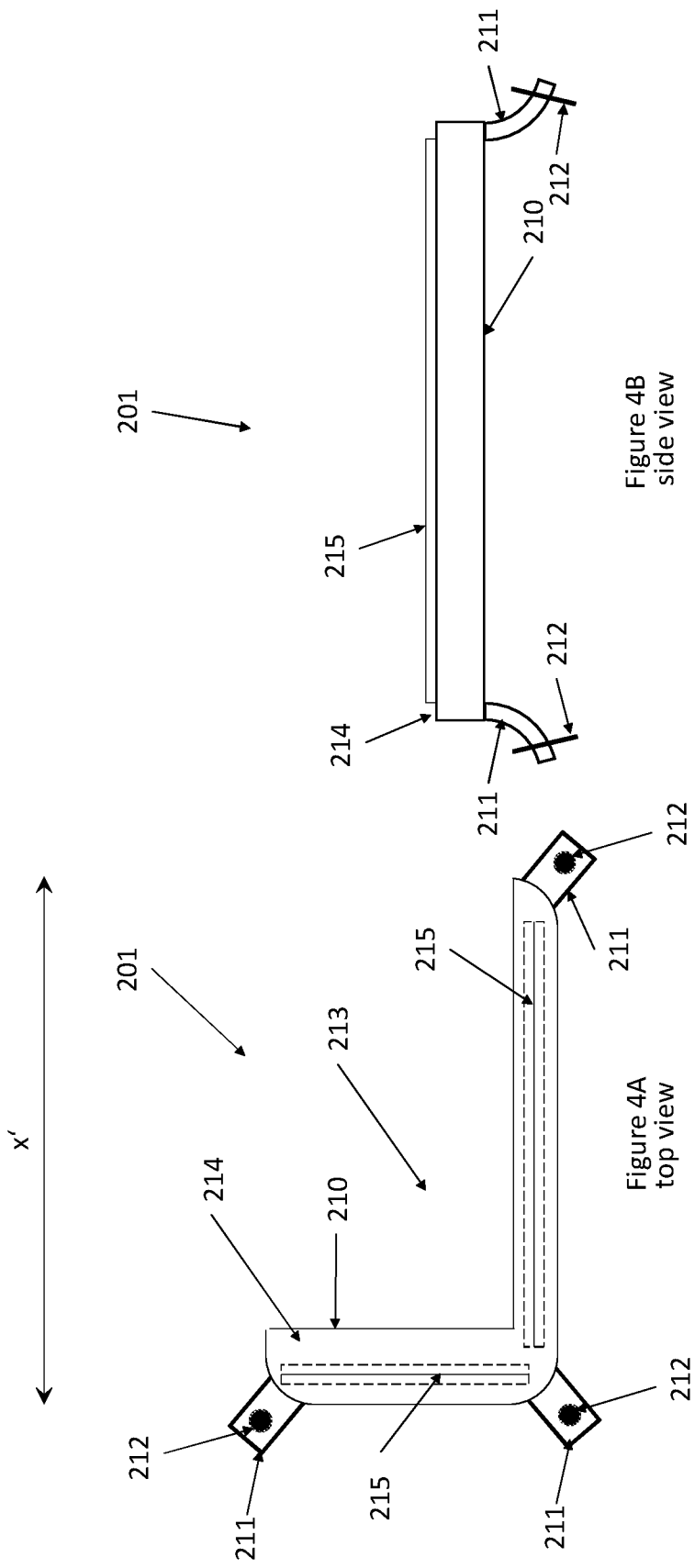

In various embodiments, there may be a position defining element on surface 214 of platform table 201 and/or plate 210, as shown in FIG. 4. This position defining element may be, for example, a longitudinal or punctate or conical elevation. In FIG. 4, this is shown as longitudinal elevations in both dimensions of the plane 415. An according recess may be milled in the bottom surface 235 of intermediate module 203 during manufacturing. Alternatively, the elevation is in bottom surface 235 and the recess may be on the platform 201 or plate 210. There may be similar elevations and recesses on/in surfaces 234 of intermediate module 203, and surface 221 of block 202.

An alternative solution of, or in combination with, providing elevations and recesses may be cylindrical pins extending out of platform table 201 and/or plate 210, and/or recesses made by drilling during the medical procedure as described above. In some cases, it may be required that intermediate module 203 is larger than plate 210 and/or block 202 in either or both dimensions of the respective surface planes such that possible shifts y and z can be realized. At least two cylindrical pins/recesses would be beneficial on each of the surfaces. In embodiments wherein the intermediate module 203 is manufactured intraoperatively during the medical process, it may be advantageous that the intermediate module 203 receives the recesses whereas the elevations (pins) are provided to platform 201/plate 210, and or block 202.

One purpose of these complementary constructional elements of elevations (pins) and recesses is so that the platform 201/the plate 210, the block 202, and the intermediate module 203 fit to each other free of play in the predetermined positions calculated, calculated, without limitation, by the processor software, to guarantee the coincidence of trajectory 251 and axis 223. In further embodiments clamps (not shown) may be used to keep all three components 201, 202, and 203 together.

In further embodiments of the invention, the surgical guidance tool described herein may be realized without an intermediate module, as shown in FIG. 8A (top view) and FIG. 8B (side view). To do so, various portions of the block 802 may be patient-specific to guarantee coincidence of the determined trajectory with axis 823 of guide aperture 822.

Illustratively, the patient-specific block 802 may have planar and non-parallel top and bottom surfaces with at least some of the heights 824, 825, 826, and 827 assuming different values. The heights 824, 825, 826 and 827 are patient-specific to ensure that the non-patient specific, predefined arrangement between the axis 823 of the guide aperture 822 and the top surface of the block 802 provides the proper predetermined angle/trajectory. Similar to above-described embodiments, the axis 823 may be perpendicular to the top planar surface 820 of the block 802. However, in other embodiments, the axis 823 may be non-perpendicular to the top planar surface 820. The bore hole 822 may be in or off the center of block 802.

There might be a trade-off between size of bore hole 222/822 and precise alignment of axis 223/823 with trajectory 251 during the trajectory e.g. into patient's skull. On one hand, bore hole 222/822 must match exactly the dimension of that part of the bore apparatus, which is moved through block 202 by the surgeon's (or a robot's) force during drilling in order to avoid an unintended angle between axis 223/823 and trajectory 251. On the other hand, the more precise the outer diameter of that part of the bore apparatus matches the inner diameter of bore hole 222/822 the higher may become the friction between these two parts. However, higher friction may increase the danger of unintended tilt of the bore apparatus during insertion such that axis 223/823 and trajectory 251 are not any more perfectly aligned. To avoid this, there may be a guiding element that may, for example, be attached to surface 220 of block 202 (alternatively, this guiding element may be integral part of block 202), which keeps the bore apparatus in an orientation such that axis 223/823 and trajectory 251 are perfectly aligned during drilling.

FIG. 9 shows a guiding element, in accordance with an embodiment of the invention. The guiding element may include guiding walls 950, with, for example, guiding rollers 951 operatively coupled to the guiding walls 950 which ensure that portion 960 of the bore apparatus moves without lateral tilt and such that axis 223/823 and trajectory 251 are always perfectly aligned during drilling. The rollers may have various shape, and generally be, without limitation, wheel shaped, circular, cylindrical or spherical in nature. Such guiding element of a bore apparatus can be advantageously utilized in connection with the systems shown, for example, in FIG. 2, compared to the invention disclosed in WO2016/198032, because the entire block 202 may be manufactured non patient-specific. Therefore, the angle of axis 223 relative to surface 220 of block 202 is independent of the patient and the guiding element can be oriented accordingly. And although, in the embodiment of FIG. 8, the block 802 is patient-specific, the angle between surface 820 and axis 823 is non patient-specific and therefore again the guiding element can easily be oriented accordingly.

The embodiments of the invention described above are intended to be merely exemplary; numerous variations and modifications will be apparent to those skilled in the art. All such variations and modifications are intended to be within the scope of the present invention.

What is claimed is:

1. A surgical guide tool comprising:
a non patient-specific platform including one or more supports configured to attach to a body part of a subject;
a non patient-specific block having a top planar surface and a bottom planar surface, the block including a guide aperture extending from the top planar surface to the bottom planar surface for guiding a surgical instrument in making at least one of a cut and a drill hole, and
an intermediate module removably positioned between the platform and the block such that the block rests on top of the intermediate module without being inserted into the intermediate module, the intermediate module having patient-specific dimensions, and configured such that the guide aperture has a desired alignment relative to the body part when the surgical guide tool is attached to the body part of the subject and the intermediate module is positioned between the platform and the block.

2. The surgical guide tool according to claim 1, wherein the guide aperture is a borehole defining an axis through the block, the axis perpendicular to both the top and bottom planar surfaces of the block.

3. The surgical guide tool according to claim 1, wherein the intermediate module has a top module surface for positioning adjacent the block, and a bottom module surface for positioning adjacent the platform, the intermediate module having a varying height between the top surface and the bottom surface, and configured such that the guide aperture has a desired alignment relative to the body part when the surgical guide tool is attached to the body part of the subject.

4. The surgical guide tool according to claim 3, wherein the top module surface and the bottom module surface are planar and non-parallel.

5. The surgical guide tool according to claim 1 wherein both the intermediate module and the platform do not block the aperture in the block when the intermediate module is positioned between the platform and the block.

6. A method comprising:
providing a non patient-specific platform configured to attach to a body part of a subject;

providing a non patient-specific block having a top planar surface and a bottom planar surface, the block including a guide aperture extending from the top planar surface to the bottom planar surface for guiding a surgical instrument;

obtaining electronic image data of an anatomical area of the subject;

determining a trajectory for at least one of a cut and a drill hole based, at least in part, on the electronic image data;

providing an intermediate module configured to be removably positioned between the platform and the block such that the block rests on top of the intermediate module without being inserted into the intermediate module, the intermediate module having patient-specific dimensions such that the guide aperture in the block is configured to guide the surgical instrument in making the at least one of a cut and drill hole along the determined trajectory when the platform is attached to the body part of the subject and the intermediate module is sandwiched between the platform and the block.

7. The method according to claim 6, further comprising:

mounting the platform on the body part, with the intermediate module sandwiched between the platform and the block; and using the guide aperture to make at least one of a cut and a drill hole into the body part.

8. The method according to claim 7, wherein the body part is the skull, wherein the platform is mounted on the skull, and wherein the guide aperture is used in guiding a surgical instrument to drill a hole through the skull into the middle ear, the method further comprising inserting an electrode array of a cochlear implant into the hole.

9. The method according to claim 6, wherein the intermediate module has a top module surface for positioning adjacent the block, and a bottom module surface for positioning adjacent the platform, the intermediate module having a varying height between the top surface and the bottom surface, and configured such that the guide aperture has the desired alignment relative to the body part when the platform is attached to the body part of the subject and the intermediate module is positioned between the platform and the block.

10. The method according to claim 9, wherein the top module surface and the bottom module surface are planar and non-parallel.

11. The method according to claim 6, wherein the guide aperture is a borehole defining an axis through the block, the axis is perpendicular to both the top and bottom planar surfaces of the block.

12. The method according to claim 6, wherein both the intermediate module and the platform do not block the aperture in the block when the intermediate module is sandwiched between the platform and the block.

* * * * *